United States Patent [19]

Henderson et al.

[11] Patent Number: 4,510,931
[45] Date of Patent: Apr. 16, 1985

[54] BARRIER FOR USE DURING CARDIOPULMONARY RESUSCITATION

[75] Inventors: Deborah Henderson, Elkton, Md.; Norman Street, Wilmington, Del.

[73] Assignee: W. L. Gore & Associates, Inc., Newark, Del.

[21] Appl. No.: 545,659

[22] Filed: Oct. 26, 1983

[51] Int. Cl.³ .............................................. A61M 16/00
[52] U.S. Cl. ............................ 128/202.28; 128/206.12
[58] Field of Search ...................... 128/202.28, 202.29, 128/203.11, 205.29, 206.12, 206.19

[56] References Cited

U.S. PATENT DOCUMENTS

| | | | |
|---|---|---|---|
| 3,861,381 | 1/1975 | Witman | 128/206.12 |
| 3,950,599 | 4/1976 | Board, Jr. | 428/236 |
| 4,025,679 | 5/1977 | Denny | 428/91 |
| 4,050,457 | 9/1977 | Davidson | 128/202.28 |
| 4,187,390 | 2/1980 | Gore | 174/102 R |

Primary Examiner—Henry J. Recla
Attorney, Agent, or Firm—Mortenson & Uebler

[57] ABSTRACT

A breathable, laminated, sanitary barrier is provided for use during cardiopulmonary resuscitation (CPR). The laminate comprises a sheet of expanded, porous polytetrafluoroethylene bonded to a substrate material. When placed over a patient's nose and mouth, the barrier enables the CPR practitioner to perform his/her mouth-to-mouth rescue attempt with substantially no reduction in air flow and eliminates direct mouth-to-mouth contact while substantially preventing the transfer of aerosols, bacteria, particles and viruses from practitioner to the patient or mannequin, or vice versa.

4 Claims, 3 Drawing Figures

U.S. Patent      Apr. 16, 1985      4,510,931
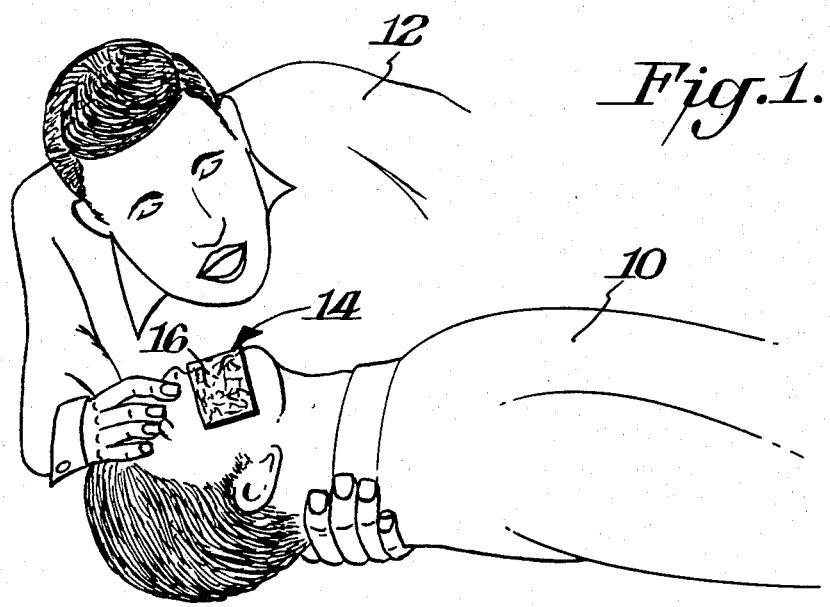
Fig. 1.
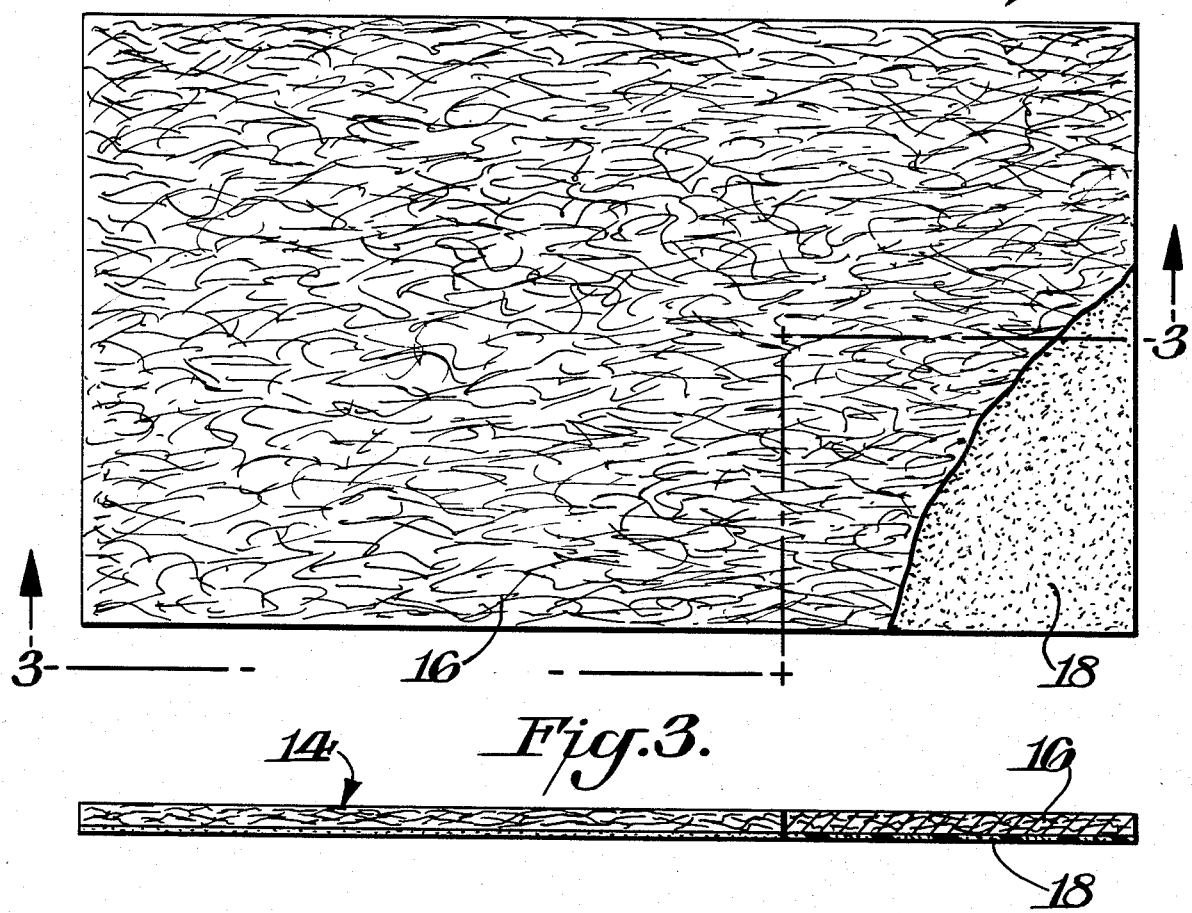
Fig. 2.
Fig. 3.

BARRIER FOR USE DURING CARDIOPULMONARY RESUSCITATION

BACKGROUND OF THE INVENTION

Potentially reversible airway obstruction, hypoventilation, apnea, blood loss, pulselessness (cardiac arrest) and brain injury are among the leading causes of death resulting from accidents, heart attacks and other medical emergencies. The leading causes of preventable sudden death before old age are ventricular fibrillation (in patients over age 44) from asymptomatic ischemic heart disease; nontraumatic accidents (e.g., drowning, poisoning); and trauma (in patients under age 38) caused by the violence of main or accidents.

Irreversible brain damage may occur when cessation of circulation (cardiac arrest) lasts longer than a few minutes or after trauma, when severe hypoemia or blood loss remain uncorrected. However, the immediate application of modern resuscitation is often capable of preventing biologic death. Resuscitative measures can be initiated anywhere without the use of equipment, by trained individuals, ranging from the lay public to physician specialists.

There were few immediately applicable effective emergency resuscitation techniques available before the 1950's, when modern respiratory resuscitation was pioneered; modern circulatory resuscitation began in the 1960's, and therapeutically promising research on brain resuscitation began in 1970. The latter work has extended to cardiopulmonary resuscitation (CPR). Resuscitation from circulatory shock has a longer history than that from cardiac arrest. Intensive care (long-term resuscitation), essential for optimal outcome after emergency resuscitation, was initiated in Scandinavia and Baltimore in the 1950's and pioneered by several groups around the world in the 1960's.

The development of modern CPR has been based largely on ideas conceived or accidently discovered many years ago, which were rediscovered and re-explored since the 1950's. These include intermittent positive pressure artificial ventilation (IPPV); mouth-to-mouth breathing; jaw-thrust; open chest cardiac resuscitation; internal defibrillation; tracheal intubation; external CPR; external defibrillation with direct current; and pathophysiologic research on dying and resuscitation.

The history of modern CPR can be summarized according to a series of landmark developments during the past 25 to 30 years: Proof that ventilation with the operator's exhaled air is physiologically sound proof of the ventilatory superiority of exhaled air ventilation (without equipment) over manual chest-pressure arm-lift maneuvers; studies showing why soft-tissue obstruction of the upper airway in unconscious patients could be prevented or corrected by backward tilt of the head, forward displacement of the mandible, and opening of the mouth; proof of the ventilatory superiority of exhaled air ventilation over chest pressure methods in children; rediscovery and development of external cardiac compression; demonstration of the need to combine positive pressure ventilation with external cardiac compression; intrathoracic electric defibrillation of the heart in human patients; the concept of the heart too good to die; external electric defibrillation of the heart in humam patients; electric cardiac pacing; proof of the feasibility of teaching CPR to the lay public; proof that lay people in the field will perform mouth-to-mouth breathing and CPR production of realistic training aids since 1960; and agreements on details of techniques and teaching methods through many national committees and international symposia.

Thus, over the past 30 years, old techniques have been refashioned into new systems. CPR works, and thousands of lives could be saved each year if enough individuals were properly trained in resuscitation. Clinical results depend heavily, however, upon perfection and uniformity of training and appropriate stress given to the importance of initiating resuscitation techniques at the earliest possible moment.

Life supporting first aid comprises basic measures, without the use of equipment, to be learned by the general public. They include selected components of CPR (head-tilt, open mouth, jaw thrust) and direct mouth-to-mouth and mouth-to-nose ventilation. They do not include external cardiac compressions (ECC). Beyond CPR, life supporting first aid includes control of external hemorrhage (by manual compression, elevation and pressure bandage); rescue pull (extrication of the victim from a wreck); and positioning to maintain open airway, combat shock and prevent further injury.

The most common site of airway obstruction is hypopharyngeal, occurring in comatose patients when the relaxed tongue and neck muscles fail to lift the base of the tongue from the posterior pharyngeal wall, when the patient's head is in the flexed or mid-position. Opening the airway is therefore the most important measure in resuscitation. Sometimes additional forward displacement of the mandible is required to produce this stretch. The combination of the backward tilt of the head, forward displacement of the mandible and opening of the mouth constitutes the triple airway maneuver. In about one-third of unconscious patients the nasal passage is obstructed during exhalation because of valvelike behavior of the soft palate; moveover, the nose may be blocked by congestion, blood or mucus. When the chin is sagging, inspiratory efforts may suck the base of the tongue into an obstructing position. Airway obstruction by the base of the tongue depends upon position of the head and jaw and can occur regardless of whether the patient is lateral supine or prone. Although gravity may aid in the drainage of liquid foreign matter; it does not relieve hypopharyngeal soft tissue obstruction, and maneuvers to lift the base of the tongue, as described above, are required.

Another cause of airway obstruction is the presence in the upper airway of foreign matter such as vomitus or blood, which the unconscious patient cannot eliminate by swallowing or coughing. Laryngospasm is usually caused by upper airway stimulation in the stuporose or lightly comatose patient. Lower airway obstruction may be the result of bronchospasm, bronchial secretions, mucosal edema, inhaled gastric contents, or foreign matter.

Airway obstruction may be complete or partial. Complete obstruction is silent and leads to asphyxia (hypoxemia plus hypercarbia) apnea, and cardiac arrest (if not corrected) within 5 to 10 minutes. Partial obstruction is noisy and must also be promptly corrected by either the patient or the rescuer, depending on the amount of air flow, as it can result in hypoxic brain damage, cerebral or pulmonary edema or other complications; and may lead to exhaustion, secondary apnea and cardiac arrest.

Emergency oxygenation of the non-intubated patient is an art that is best acquired through guided clinical experience. Measures for emergency airway control are being improved continuously. These measures should be practiced to perfection on manikins.

Recognition of acute airway obstruction must go hand in hand with therapeutic action, step by step, taking into account the number of personnel available, their training and the possible complications of various therapeutic maneuvers. The airway control measures are intended primarily for the unconscious patient whose treatment requires rapid stepwise progression until the obstruction is controlled.

If the victim is unconscious, backward tilt to the head, forward displacement of the mandible, or both, prevent hypopharyngeal obstruction by the base of the tongue. Either maneuver stretches the tissues between the larynx and mandible, and thereby lifts the base of the tongue from the posterior pharyngeal wall.

Emergency oxygenation attempts in the unconscious patient should start with backward tilt of the head (and/or, in addition, if necessary, jaw thrust and opening of the mouth). If the airway remains obstructed, with or without breathing efforts, add positive pressure inflation attempts.

For direct mouth-to-mouth ventilation using head-tilt and/or jaw thrust, the practitioner should position himself at the side of the patient's head.

Backward tilt of the head, jaw thrust and opening of the mouth can be practiced on manikins, and patients who require artificial ventilation.*

*This background material has been derived from Safer, P. Cardiovascular Cerebral Resuscitation, Stavanger, Norway, Asmund S. Laerdal, Philadelphia PA, Saunders (Dist.) (1981), World Federation of Anesthesiologists.

Until now, inextricably associated with the practice of CPR has been the often unpleasant and unavoidable direct mouth-to-mouth contact between victim and CPR practioner.

SUMMARY OF THE INVENTION

The invention comprises the use of a laminate of expanded, porous polytetrafluoroethylene bonded to a porous fabric substrate during cardiopulmonary resuscitation, the laminate acting as a sanitary barrier between the mouth of the victim and the mouth of the CPR practitioner. The substrate is preferably a nonwoven synthetic material selected from the class consisting of polyesters, polyethylene, polypropylene and polyamides. The preferred substrate material is nonwoven polyester.

BRIEF DESCRIPTION OF THE DRAWINGS

FIG. 1 is a pictorial view of the barrier of this invention in use during CPR.

FIG. 2 is a top plan view of the barrier of this invention, shown partly broken away.

FIG. 3 is an elevational view of the barrier of this invention, partly in cross-section, taken substantially along the line 3—3 of FIG. 2.

DETAILED DESCRIPTION OF THE INVENTION AND PREFERRED EMBODIMENTS WITH REFERENCE TO THE DRAWINGS

A breathable, laminated, sanitary barrier is provided for use during cardiopulmonary resuscitation. The laminate comprises a sheet of expanded, porous polytetrafluoroethylene bonded to a substrate material. When placed over a patient's nose and mouth, the barrier enables the CPR practitioner to perform his/her mouth-to-mouth rescue attempt with substantially no reduction in air flow and eliminates direct mouth-to-mouth contact while substantially preventing the transfer of aerosols, bacteria, particles and viruses from practitioner to the patient or mannequin, or vice versa.

The barrier of this invention is a laminate of expanded, porous polytetrafluoroethylene (EPTFE) bonded to a substrate. To date, a laminate of 4 in. by 7 in. has been satisfactory, but it should be clear that dimensions are not critical. The EPTFE, which is a key element to the invention, preferably has an average pore opening size of about 10–15 micrometers and a minimum Frasier Number of about 40, the thickness of the sheet being about 0.001 inch. The EPTFE is available commercially from W. L. Gore & Associates, Inc., Elkton, Md., sold under the trademark GORE-TEX ®. Its basic properties are disclosed in U.S. Pat. No. 4,187,390.

The substrate bonded to the EPTFE to form the laminate of this invention provides desirable drape and handling convenience. To date, the preferable substrate has been nonwoven polyester fabric having a thickness of about 0.007 inch. A suitable nonwoven polyester is commercially available from the Pellon Corporation, Philadelphia, PA, sold under the trademark "AXCEL". One skilled in the art will know that other substrates can be used, including woven or nonwoven synthetics such as polyesters, polyethylenes, polypropylene and polyamides. Some natural fabrics may be suitable.

The substrate is preferably heat-bonded to the EPTFE, although an adhesive or other bonding method could be employed.

The barrier in use according to this invention is placed over the victim's (or mannequin's) mouth as shown in FIG. 1 and CPR then proceeds as before. Preferably the barrier is placed such that the EPTFE contacts the victim and the fabric contacts the practitioner, but the reverse configuration is also effective.

FIG. 1 shows the CPR practitioner 12 applying mouth-to-mouth resuscitation to a victim 10 through the barrier 14 of the invention.

FIG. 2 shows the barrier 14 of this invention comprising the substrate 16 bonded to the EPTFE 18, shown in the portion broken away.

FIG. 3, taken substantially along the line 3—3 of FIG. 2, shows the laminate in elevation. The preferred nonwoven substrate 16 is bonded to the EPTFE 18, as can be seen most clearly in the cross sectional view.

The invention virtually overcomes the antipathy and unpleasantness to CPR practitioners arising from direct mouth-to-mouth contact with strangers (or mannequins used by others). The laminate is clean and sanitary and, if desired, may be sterilized. Breathing through the laminate is substantially unhindered because of the very high porosity of the EPTFE. The barrier substantially prevents the transfer between victim and practitioner of the following: aerosols, particles, bacteria, viruses such as herpes, blood, vomitus, alcohol, injested poisons, other chemicals and acids which may have accidentally been swallowed, water and smoke.

While the invention has been disclosed herein in connection with certain embodiments and detailed descriptions, it will be clear to one skilled in the art that modifications or variations of such details can be made without deviating from the gist of this invention, and such modifications or variations are considered to be within the scope of the claims hereinbelow.

What is claimed is:

1. During cardiopulmonary mouth to mouth resuscitation, using by placing a laminate of expanded, porous polytetrafluoroethylene bonded to a porous fabric substrate, the laminate acting as a sanitary barrier between the mouth of the victim and the mouth of the CPR practitioner.

2. The method of claim 1 wherein said substrate is a nonwoven synthetic material.

3. The method of claim 2 wherein the substrate material is selected from the class consisting of polyesters, polyethylene, polypropylene and polyamides.

4. The method of claim 3 wherein the substrate material is a nonwoven polyester.

* * * * *

UNITED STATES PATENT AND TRADEMARK OFFICE
CERTIFICATE OF CORRECTION

PATENT NO. : 4,510,931

DATED : April 16, 1985

INVENTOR(S) : Deborah Henderson and Norman Street

It is certified that error appears in the above-identified patent and that said Letters Patent is hereby corrected as shown below:

In column 1, line 15, please change "main" to --man--.

Signed and Sealed this

Third Day of September 1985

[SEAL]

Attest:

DONALD J. QUIGG

Attesting Officer     Acting Commissioner of Patents and Trademarks - Designate